United States Patent [19]

Trachtman

[11] 4,162,828
[45] Jul. 31, 1979

[54] APPARATUS AND METHODS FOR DIRECTLY MEASURING THE REFRACTION OF THE EYE

[76] Inventor: Joseph N. Trachtman, 57 Hicks St., New York, N.Y. 11201

[21] Appl. No.: 838,107

[22] Filed: Sep. 30, 1977

[51] Int. Cl.² .............................................. A61B 3/10
[52] U.S. Cl. ........................................ 351/9; 351/13; 351/14; 351/39
[58] Field of Search ..................... 351/6, 7, 13, 14, 39, 351/9; 356/5

[56] References Cited

U.S. PATENT DOCUMENTS

| | | | |
|---|---|---|---|
| 3,136,839 | 6/1964 | Safir | 351/6 X |
| 3,536,383 | 10/1970 | Cornsweet et al. | 351/6 |
| 3,715,166 | 2/1973 | Leighty et al. | 356/125 |
| 3,888,569 | 6/1975 | Munnerly et al. | 351/39 X |

OTHER PUBLICATIONS

Niles Roth, "Recording . . . Optometer," *Am. J. Optom & Arch . . .*, vol. 39, No. 7, pp. 356–361, Jul. 1962.

F. W. Campbell et al., "High . . . Optometer," *JOSA*, vol. 49, No. 3, Mar. 1959, pp. 268–272.
J. Warshawsky, "High . . . Accommodation", *JOSA*, vol. 54, No. 3, Mar. 1964, pp. 375–379.
Charles Riva, "New . . . Reflectometer", *Applied Optris*, vol. 11, No. 8, Aug. 1972, pp. 1845–1848.

*Primary Examiner*—Paul A. Sacher
*Attorney, Agent, or Firm*—Marn & Jangarathis

[57] ABSTRACT

Optometer apparatus for directly measuring the refraction of the eye and methods therefor are provided in accordance with the teachings of the present invention. According to an exemplary embodiment of the present invention, a double slit, Scheiner principle projection system is employed to project an image upon the retina. The retinal image is then focused upon an optoelectric, linear sensor which provides an output corresponding to the intensity gradient of the retinal image focused thereon. The output of the optoelectric, linear sensor may then be employed as a measure of the refraction of the eye.

9 Claims, 1 Drawing Figure

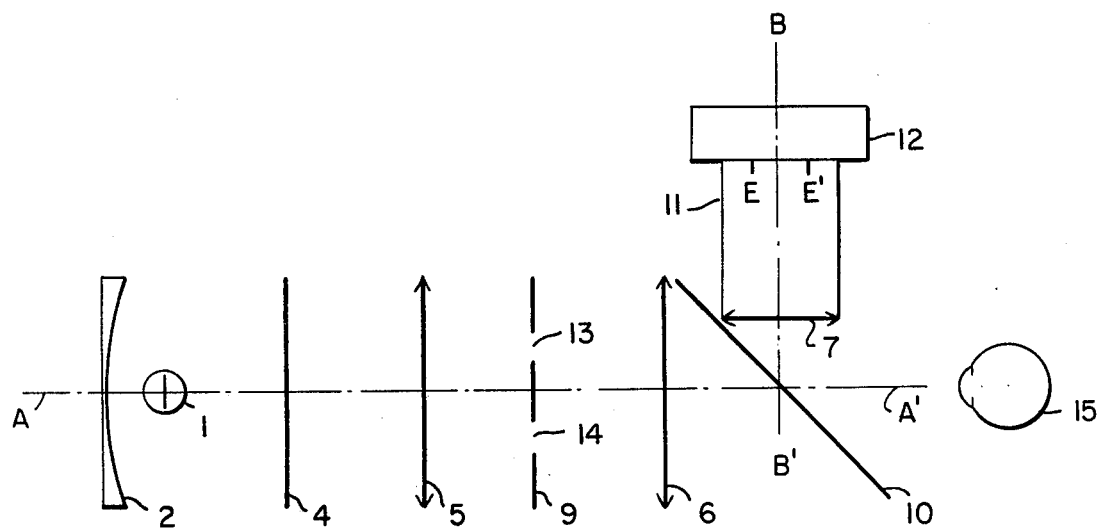

APPARATUS AND METHODS FOR DIRECTLY MEASURING THE REFRACTION OF THE EYE

This invention relates to an optical system for testing the eye and more particularly to high speed, infrared optometer apparatus for measuring the refraction of an eye.

GENERAL DESCRIPTION

Direct measurement of the refraction of the eye has long been sought in order to replace the subjective exchange procedures now generally employed between doctor and patient. While optical systems and instruments directed to this purpose are available, the same are generally excessive in cost and are characterized by certain disadvantages which have thus far prevented wide adoption.

Conventional optical systems for directly measuring the refraction of the eye each attempt to measure the ability of the cornea and lens to sharply focus an image upon the retina. This is typically achieved by the displacement, under servo control, of an imaging source, imaging lenses, and/or imaging targets and thereafter measuring the relative location of these elements with respect to a norm to determine the refraction of the eye or what is commonly known as the prescription. Proper focus is ascertained through techniques of determining when displacement of an imaging source no longer induces displacement of an illuminated spot on the retina or through applications of the principle that an emmetropic eye will focus a single image on the retina while an ametropic eye forms a pair of images upon the retina which have a proportional displacement therebetween.

The displacement techniques employed in prior art optical systems for directly measuring the refraction of the eye generally rely upon high speed servo mechanisms which are both excessively costly and disadvantageous because the moving parts associated therewith adversly reflect upon system reliability. Furthermore the null balancing techniques generally utilized therewith to achieve the focus at which the refraction of the eye can be measured does not readily lead to a high speed system. In addition, conventional optical systems for directly measuring the refraction of the eye typically rely upon infrared light sources which emit a substantial quantum of light and this in turn frequently mandates cooling of the sensors employed as well as increased costs associated therewith. Patient discomfort is also frequent and the equipment per se requires frequent maintenance and cleaning. Thus for these reasons direct reading optical systems for measuring the refraction of the eye have not gained wide acceptance or usage and subjective exchange procedures between doctor and patient remain the most prevalent form of measuring the refraction of the eye to obtain the patient's prescription.

Therefore, it is an object of this invention to provide improved optometer apparatus and methods therefor for measuring the refraction of the eye.

An additional object of this invention is to provide highly reliable optometer apparatus having no moving parts.

A further object of this invention is to provide optometer apparatus employing measurement techniques requiring low level source intensities and sensors not requiring cooling.

Another object of this invention is to provide direct reading optometer apparatus wherein myopic refraction is readily distinguishable from hyperopic refraction.

An additional object of this invention is to provide direct reading optometer apparatus employing measurement techniques not requiring an assumption as to the chromatic aberration of the eye for infrared radiation.

Other objects and advantages of this invention will become clear from the following detailed description of an exemplary embodiment thereof, the novel features will be particularly pointed out in conjunction with the appended claims.

In accordance with this invention optometer apparatus is provided wherein a double slit, Scheiner principle projection system is employed to project an image upon the retina; the retinal image is then focused onto an optoelectric linear sensor means which provides an output corresponding to the intensity gradient of the retinal image focused thereon; and the output of the optoelectric linear sensor means is employed as a measure of the refraction of the eye. The invention will be more clearly understood by reference to the following detailed description of an exemplary embodiment thereof in conjunction with the accompanying drawing in which:

The FIGURE schematically illustrates an exemplary embodiment of optometer apparatus in accordance with the present invention.

DESCRIPTION OF THE EXEMPLARY EMBODIMENT

Referring now to the FIGURE there is schematically illustrated an exemplary embodiment of optometer apparatus in accordance with the teachings of the present invention. The optometer apparatus illustrated in the FIGURE acts, in essence, to employ the Scheiner principle to project two slits of parallel light in Maxwellian view into the eye. For an emmetropic eye a single slit will result in being focused on the retina while for an ametropic eye a pair of slits will be focused on the retina having a proportional separation which corresponds to the refraction of the eye. Thus, the displacement between these slits may be employed as a direct measurement of the refraction of the eye and what is commonly known as the prescription may be developed directly therefrom. The retinal image formed is then focused onto a sensor which scans at a sufficiently high rate to minimize most accommodation problems and the sensor is configured as a linear array so that a Gaussian energy distribution of the retinal image is produced therefrom. The Gaussian energy distribution of the retinal image may then be employed to produce a direct read out of the refraction of the eye. The invention employs an infrared transmitting, visible light absorbant filter so that the light source is barely visible to an observer and since no nulling system is employed, no assumption of the chromatic aberration of the eye for infrared light is necessary.

Referring more particularly to the FIGURE, the embodiment of the invention illustrated therein comprises a source 1, mirror means 2, filter means 4, lens means 5-7, double slit means 9, beam splitter means 10, tube means 11, and sensor means 12. The source means 1 preferably takes the form of a tungsten lamp having a ribbon filament so that the same acts as a single slit source of white light. The mirror means 2 is disposed behind the source 1 and takes the form of a concave mirror which is axially displaced behind the source means 1 so that the source means 1 resides slightly beyond the focal length of the mirror means 2. Thus, in this manner, as well known to those of ordinary skill in the art, light emanating from the rear surface to the source 1 is reflected from the concave side of the mirror in a manner so that light rays coming from the rear of the source 1 are imaged by the mirror means 2 at the plane of the source means 1 increasing the intensity of the source thereby.

The filter means 4 takes a form of an infrared transmitting filter which acts, in the well known manner to absorb visible light below approximately 850 nm so that infrared light is passed therethrough toward the lens means 5. The use of infrared light for measurement purposes is important as the same tends to avoid accommodation problems associated with the eye. More particularly, it has been established that the latency of an accommodation change can vary from 100 to 300 milliseconds and the change can occur with a velocity of about 5 diopters per second. Therefore, if the desired resolution was to be 0.12 diopter, the optometer would have to measure accommodation at least once each 25 milliseconds to achieve a continuous monitoring of the accommodative changes. To avoid sampling rates which are this high, the light source of the optometer is selected to be in the infrared region so as to be invisible and hence not as a stimulus to accommodation. Furthermore, the development of the infrared radiation through the filter means 4 in the manner illustrated in the FIGURE is advantageous in that much of the heat associated with the direct ultilization of an infrared source of radiation is avoided. It should be noted, however, that the infrared filter means 4 still allows some visible light to pass therethrough so that the subject observes a red glow which is neither annoying nor capable of causing harm. If it is assumed for the exemplary embodiment being described that the concave mirror means 2 has a focal length of approximately 38 millimenters so that the same is displaced a distance of 39 millimeters behind the source 1, the infrared filter means 4 may be displaced, for example, 80 millimeters in front of the source means 1. Accordingly, it will be appreciated that the infrared filter means 4 receives divergent white light radiation from the front portion of the source 1 and divergent white light radiation from the rear portion of the source means 1 that has been reflected by the concave mirror means 2 to provide infrared radiation to the lens means 5.

The lens means 5 and 6 may take the form of achromatic convex lenses well known to those of ordinary skill in the art which act as a pair to collimate radiation passing therethrough. In the case of the lens means 5 and lens means 6, divergent infrared radiation from the infrared filter means 4 is received and rendered parallel in the well known manner so that infrared light is further supplied to the double slit means 9. For the displacement values given above, the convex lens means 5 is displaced from the infrared filter means 4 by a distance which may typically be 95 millimeters and in front of the double slit means 9 by an exemplary distance of 65 millimeters.

The double slit means 9 may take any of the conventional forms of optical slit devices well known to those of ordinary skill in the art such as an optical plate having a pair of slits 13 and 14 therein. The slits 13 and 14 within the double slit means 9 should be symmetrically disposed about the optical axes A—A' of the optometer apparatus being described and for appropriate operation within the Scheiner principle, the slits should be displaced from one another by a distance which when imaged in the plane of the pupil of the eye will be less than the diameter of the pupil of the eye. A typical displacement for one millimeter slits within the double slit means 9 may be approximately 1.5 millimeters. Accordingly, convergent infrared radiation supplied to the double slit means 9 from the infrared filter means 4 and the convex lens means 5 is passed through the slit means 13 and 14, in the well known manner so as to be applied to the lens means 6.

The lens means 6 is an achromatic convex lens, as aforesaid, which acts to collimate the radiation issued from lens means 5 and to focus the slits through the beam splitter means 10 at the plane of the pupil of the eye 15 illustrated in the FIGURE. If, for the exemplary value set forth above, the double slit means 9 is displaced in front of the lens means 5 by a distance corresponding to approximately 65 millimeters, the lens means 6 would be positioned in front of the double slit means 9 by a distance of approximately 90.6 millimeters. Furthermore, the eye would be positioned so that the plane of the pupil thereof resides in a typical case at a distance of 207 millimeters from the lens means 6 so that each of the slits 13 and 14 within the double slit means 9 could be imaged thereon. Accordingly, it will be appreciated that the source 1, mirror means 2, filter means 4 and lens means 5 and 6 act to supply collimated infrared radiation to the eye 15 while the double slit means 9 and the lens means 6 act to focus the images of the pair of slits 13 and 14 onto the plane of the pupil of a subject's eye 15. In this manner, the Scheiner principle is employed to project two slits of parallel light in Maxwellian view into the eye and image the same at the pupil thereof. For the exemplary embodiment of the optometer apparatus being described herein, the concave mirror 2 may have a focal length of 38 millimeters, the lens means 5 may have a focal length of 63 millimeters and the convex lens means 6 may have a focal length of 88 millimeters. Similarly, the double slit means 9 may have slits 13 and 14 displaced by 1.5 millimeters and each slit may take the form of a 1 millimeter slit.

The two slits of light focused on the plane of the pupil in Maxwellian view, as aforesaid, are imaged back onto the retina as well known to those of ordinary skill in the art. If the eye 15 is emmetropic and also has no accommodation, a single slit of light will be formed on the retina in accordance with Scheiner's principle. However, if the eye 15 is ametropic a pair of slits will be formed on the retina having a proportional separation therebetween which correspondes to the refractive error in eye. More particularly, as well known to those of ordinary skill in the art, for a myopic condition the image of each slit will converge before the retina and hence the retinal image corresponding to the pair of slits which are separated depending upon the degree of the myopic condition. Conversly, for hyperopia, a single image of the pair of slits will be formed behind the retina and for this reason a pair of slits will be formed on the retina in response to this condition. In each case of a double slit image on the retina, the displacement therebetween will correspond to a measure of the refraction of the eye which can be directly translated into the appropriate prescription necessary for correction. Accordingly, it will be appreciated by those of ordinary skill in the art that in response to the imaging of the pair of slits on the plane of the pupil of the eye 15, a retinal image is formed which corresponds to either a single slit for an eye which is emmetropic and has no accommodation or a double slit for an eye exhibiting a change, either an increase or a decrease, in refraction associated with an ametropic condition.

The retinal image formed is reflected back onto the beam splitter means 10. The beam splitter means 10 may take any of the conventional forms of this common class of device well known to those of ordinary skill in the art and acts in the well known manner to pass radiation from the lens means 6 therethrough for imaging at the pupil of the eye 15, while radiation reflected back from the eye 15 is communicated by the beam splitter means 10 toward the lens means 7. The beam splitter means is displaced from the plane of the pupil of the eye by a distance which may typically correspond to 132 millimeters as measured along the central axis A—A' of the device and acts in the well known manner to direct radiation corresponding to that reflected from the retina image in the eye towards the lens means 7.

The lens means 7 may also take the form of an achromatic convex lens having a focal length, for the exemplary values set forth above, which may typically be 88 millimeters. In addition, the lens means 7 may be disposed by a distance of 44 millimeters above the axis A—A' in such manner that its central axis corresponds to the point of intersection with the axis A—A' and the beam splitter means 10. Accordingly, the retinal image is communicated from the beam splitter means 10 through the tube means 11 and imaged upon the sensor means 12.

The tube means 11 functions in the well known manner to prevent spurious light from being introduced into retinal image radiation being conveyed from the lens means 7 to the sensor means 12. In addition thereto, the length of the tube means 11 is delibertly selected so the same exceeds the focal length of the lens means 7 so that the conjugate of the retinal image is formed on the sensor means 12 in such manner, that a discrete range of retinal images is representative of a hyperopic or farsighted condition while a second discrete range of images is representative of a myopic or nearsighted condition. More particularly, while the function of the tube means 11 is principally to isolate retinal image radiation being conveyed through the lens means 7 from ambient radiation to enhance the sensitivity of the sensor means 12 and hence improve the signal-to-noise ratio of the output thereof, the length of the tube means 11 and the focal length of the lens means 7 determine the nature of the image radiation imposed on the sensor means 12. Thus for instance, if the length of the tube means 11 were selected to be identical to the focal length of the lens means 7, the retinal image would be formed directly at the surface of the sensor means 12 in such manner as to directly correspond to the retina image formed at the eye 15 and hence provide no indication whatsoever in the case of an ametropic eye as to whether or not a myopic or hyperopic condition were being measured. For example, in the case of an emmetropic eye exhibiting no accommodation, a single image of the slit would be formed on the retina as aforesaid and accordingly a single image of the slit retinal image would be formed at the surface of the sensor means 12 at the axis B—B'. However, for an ametropic condition, wherein two slits form the retinal image, the distance between the slits is proportional to the correction required regardless of whether or not a myopic or hyperopic condition is present. Thus, were the length of the tube 11 equal to the focal length of the convex lens means 7, while the distance between the pair of slits formed would be a measure of the refraction of the eye, no clear indication as to whether a myopic or hyperopic condition is present would be indicated.

It would be apparent however that for a myopic condition, diverging radiation forms the retinal image, while conversely, for a hyperopic condition convergent radiation forms the retinal image. This means that if the length of the tube means 11 is made to be less than or greater than the focal length of the lens means 7, the characteristic divergent or convergent radiation employed to form the image for a myopic or hyperopic condition, respectfully, may be employed to distinguish therebetween. Thus it will be appreciated by those of ordinary skill in the art that in the case of the length of the tube means 11 being less than the focal length of the lens means 7, the divergent nature of the pair of slits formed on the retina due to a myopic condition will cause images associated with a myopic condition to fall within a certain range E—E' at the surface of the sensor means 12 and conversely pairs of slits associated with a hyperopic condition will cause image radiation associated with the pair of slits formed to fall outside of the range E—E' at the surface of the sensor means 12.

Conversely, should the length of the tube means 11 be greater than the focal length of the lens means 7 a conjugate image will be formed at the surface of the sensor means 12 so that image radiation associated with the pair of slits from a hyperopic condition will fall within the range E—E' while image radiation associated with a pair of slits from a myopic condition will fall external to the range annotated E—E' at the surface of the sensor means 12. The actual range E—E' will vary with respect to the relationship between the length of the tube means 11 and the focal length of the lens means 7. In a preferred embodiment of the instant invention which was built and tested the length of the tube means 11 was selected to be 105 millimeters when the focal length of the lens means 7 was 88 millimeters. The conjugate image formed by a tube means 11 having a length which is longer than the focal length of the lens means 7 is preferred since optical packaging is facilitated thereby and sensor contamination from radiation being focused on the pupil is more readily avoided. However, it will be appreciated by those of ordinary skill in the art that the utilization of a tube means 11 having a shorter or equal length to the focal length of the lens means 7 could be employed as well.

The sensor means 12 may take the form, for this embodiment of the present invention, of a linear, charge coupled device or the like which acts in the well known manner to receive radiation corresponding to a gradient and to provide a plurality of voltage outputs as a preselected scanning rate which correspond to the intensity gradient received along the sensor means 12. More particularly, the sensor means 12 may take the form of a linear array of photodiodes or the like which act as a line scanner for light intensity along the narrow area defined by the aperture of the tube means 11. While operation of such a line scanner in a charge coupled or charge storage mode is preferred due to the ready availability of commercial devices of this type, it will be appreciated by those of ordinary skill in the art that other sensor means could be employed as well so long as the sensor geometry is such that a large number of discrete outputs may be obtained along the length thereof to produce an output voltage corresponding to a point to point representation of the intensity imposed thereon.

In an exemplary embodiment of the instant invention which was built and tested, the sensor means 12 took the form of a charge coupled device having 512 photodiodes configured in a ½ inch linear array which was arranged to scan once every 30 milliseconds and produce an output of from 0–5 volts for each of the 512 photodiodes therein. The sensor means 12 per se may be conventional and take the form, for instance, of a Model RL512 C photodiode array such as is manufactured by Reticon Corporation of 910 Benicia Avenue, Sunnyvale, Ca. This array was employed in conjunction with a Reticon Model RC400 Mother Board and a Model RC402 Driver/Amplifier Board. The mother board contains, as well known to those of ordinary skill in the art, clock and counter circuits and logic to generate appropriate clock pulses, as well as a socket to accept the driver/amplifier board. The video output available from the driver/amplifier board may be employed in conjunction with a Reticon Cash-1B Video Amplifier Sample And Hold circuit for further processing for purposes of applying the resultant output signal to a scope or computer from which the output can be calibrated in terms of actual prescription. Alternatively, a video amplifier formed of op-amps which are so configured as to provide a 0–5 volt output may be substituted for the Cash-1B Video Amplifier Sample and Hold circuit to provide a voltage output for the sensor means 12 which varies on a per diode basis from 1–5 volts.

The charge coupled linear array, the driver amplifier, the mother board and the video amplifier as described above as suitable for use in the present invention are fully described in Reticon publications devoted thereto and need not be further set forth herein. It is sufficient therefore to appreciate that the retinal image focused onto the sensor means 12 is transduced by each of the 512 photodiodes therein, at a scanning rate corresponding to one scan for each 30 milliseconds, so that an output is produced from each photodiode which varies in accordance with the intensity of the radiation imposed thereon. Accordingly, the final output of the sensor means 12 will take the form of the Gaussian energy distribution of the retinal image which may then be supplied to a scope or a computer for direct correlation in terms of the refraction of the eye measured, to thus correspond to the appropriate prescription required for the patient. The use of the linear charge coupled array described above is highly advantageous in that not only does the same provide a direct reading of the refraction of the eye but the representative Gaussian energy distribution obtained of the retinal image is highly precise in that the signal-to-noise ratio of the device has been calculated in the range of one thousand-to-one. In this manner, the sensor means 12 provides an output which will correspond either to a sharply defined imaging of a single slit on the axis B—B' thereof, indicative of an emmetropic eye or an energy distribution corresponding to the focusing of a pair of slits thereon. Furthermore, due to the distal placement of the sensor means 12 associated with the disproportionate length of the tube means 11 to the focal length of the lens means 7, a spatial distribution for a conjugate image of a pair of slits between the locations indicated as E—E' will indicate a hyperopic condition while a spatial distribution outside the locations E—E' will indicate a myopic condition. Thus, either a single slit or a double slit whose displacement precisely indicates the refraction of the eye is obtained as an output of the sensor means 12.

In operation of the exemplary optometer apparatus illustrated in the FIGURE, radiation from the light source 1, which corresponds to a ribbon filament tungsten lamp, is applied from the rear of the source 1 to the mirror means 2 and from the front of the source directly to the filter means 4. The radiation applied to the mirror means 2 is focused in the plane of source 1 and applied to the filter means 4 so that the same is added to the radiation supplied directly thereto from the front of the source 1. The filter means 4 absorbs visible light below 850 nm and transmits infrared energy to the convex lens means 5 where such radiation is made less divergent as aforesaid. Thereafter, radiation from the lens means 5 is applied to the double slit means 9 so that a pair of slits are imaged onto the lens means 6. This radiation is collimated and focused through the beam splitter means 10 directly onto the plane of the pupil of the eye 15 by lens means 6. The radiation level imaged onto the plane of the pupil is thus essentially limited to the infrared range so that while the infrared filter means 4 passes some visible spectrum through to the subject, only a sufficient amount of visible radiation is passed for the subject to observe a red glow. In a typical embodiment of the instant invention which was built and tested irradiance was measured at approximately 4 microwatts per centimeter square. The radiation from the pair of slits 13 and 14 is then imaged by convex lens means 6 onto the plane of the pupil of the eye and forms an image on the retina which is a function of the refraction of the eye 15, as aforesaid.

If the eye is emmetropic a single slit will be formed on the retina at the axis A—A' while if an ametropic eye is being tested a pair of slits will be formed on the retina whose separation is proportional to the correction required, as aforesaid. The retinal image thus formed is applied by the beam splitter 10 to the convex lens means 7 and through the tube means 11 to the surface of the sensor means 12. Due to the utilization, in the preferred embodiment, of a tube means 11 whose length is greater than the focal length of the lens means 7, the conjugate of the retinal image is formed on the surface of the sensor means 12. Thus, the distal displacement of the sensor means 12 will not effect the image location of a single split retinal image, however; the converging and divergent radiation associated with a retina image consisting of a pair of slits is readily discernable in that converging radiation associated with a hyperopic condition will be imposed within the range indicated as E—E' while divergent retina image information associated with a myopic condition will fall without the range E—E'. The sensor means 12 scans, as aforesaid, once each 30 milliseconds and will produce outputs from zero volts to maximum voltage range for each of the 512 photodiodes therein. Thus the output of the sensor means 12 will correspond to a scan of the Gaussian energy distribution of the retinal image applied to the sensor means 12 wherein a maximum voltage corresponds to the central location of the slit image and the spatial distribution thereof with respect to the axis B—B' corresponds to the refraction of the eye or the correction required.

In actual operation, the charge coupled device corresponding to the sensor means 12 is highly stable in a temperature range of from 60°–80° F. after a warm-up time of approximately one hour. Furthermore, for the exemplary values or ratings employed in the exemplary embodiment, no cooling of the sensor means 12 is required and of course the design of the instant optometer apparatus does not require an asumption of the chromatic aberration of the eye since a null balancing system is not utilized. This is highly advantageous since in a nulling system, each differing amount of chromatic aberration for each different eye requires a resetting of the null point.

The output of the sensor means 12 may then be applied to a scope or computer so that such output may be correlated directly into the refraction of the eye being measured or the necessary prescription appropriate for the patient under test. All this transpires absent so much as a single lens replacement or a single inquiry to the subject as to whether or not a given set up was better or worse than that which proceded it so that direct measurement of the refraction of the eye is quickly and easily achieved without any patient discomfort or subjective inquiries. Futhermore, the sampling rate employed in the instant optometer apparatus may be relied upon to continuously monitor accommodation in an objective, reliable, and valid manner. While the scanning rates here described are not so fast as to be sufficient for all studies of accommodation, alternate sensor means and clocking rates may be substituted for those described in an effort to achieve sufficient speed to continuously monitor accommodative changes under all conditions. For usual purposes, however, a scanning rate which is sufficient to continuously monitor all accommodative changes is not required since the instant optometer apparatus employs an infrared region light source which is not a stimulous to accommodation and hence is suitable for the direct measurement of the accommodation of the eye.

CONCLUSION

The optometer apparatus according to the instant invention is viewed as highly advantageous in that the same avoids the use of high intensity sources which frequently impose subject discomfort as well as cooling requirements for any sensory equipments employed. In addition, servo systems and the nulling techniques are completely avoided to render the subject optometer apparatus highly reliable while much less costly to produce. While the invention has been disclosed in regard to a rather specific embodiment thereof it will be apparent to those of ordinary skill in the art that the teachings herein may be varied to provide for other specific applications as well as extended to achieve other purposes. For instance, while the instant invention has been disclosed in association with a sensor means which corresponds to a linear, charged coupled array capable of measuring slit displacement along only a single axis; the teachings contained herein need not be limited to measuring solely the refraction of the eye along such single axis to thus obtain only a direct measurement of the normal, hyperopic or myopic condition associated with the retina image. Thus, the total refraction of the eye, including any astigmatic condition associated therewith could be measured by apparatus conforming to the teachings of the instant invention by the substitution of a square or circular photodiode array for the linear array disclosed. Accordingly, if a 512×512 or 1024×1024 diode array were utilized for the linear sensor described herein, total refraction of the eye could be measured as a function of the total spatial distribution provided as an output of the sensor means. Under these conditions, the total refraction of the eye could be measured along the same principles said forth above wherein the axial measurement would correspond to the myopic or hyperopic condition and the off-axis measurement would define the astigmatic condition. Should total refraction be desired to be measured in the manner described above, more substantial infrared intensities would be required and the same could be obtained, for example, by employing a pulse diode array as the source to obtain the required irradiance.

Similarly filed while the optometer apparatus disclosed herein has been described for the principle purpose for monitoring retinal reflections, the optometer apparatus could be used for monitoring other aspects of the eye such as the position of the eye. For instance rather than monitoring retinal reflections as imaged on the sensor means 12 cornial reflection could be imaged onto the sensor means for the purpose of monitoring eye position. This could be simply and readily achieved by either a displacement of the double slit means 9 away from the eye to such distance that the image of the double slit is focused onto the cornea rather than on the plane of the pupil. Alternatively, the lens means 7 could be displaced so that corneal reflections were focused onto the sensor means 12 rather than a retinal image. Furthermore, a combination of displacement of the double slit means 9 and the lens means 7 could be relied upon to achieve this result. Once corneal reflections were focused onto the sensor means 12 rather than the retinal reflection, read out of the sensor means 12 would serve as a measurement of eye position which could then be monitored on a continuous or discontinuous bases using essentially the same apparatus as disclosed herein.

In addition, it should be noted that while the instant invention has been disclosed in conjunction with rather specific values for the exemplary embodiment, many modifications and variations in both the nature of the equipments employed and the specific optical parameters set out may be implemented by those of ordinary skill in the art to facilitate specific designs, applications or objectives. Furthermore, while not forming a specific part of the instant invention, various digital techniques may be relied upon in achieving a calibration of the output of the sensor means 12 in terms of the prescription required.

Although the invention has been described in connection with a highly specific exemplary embodiment thereof, it will be understood that many modifications and variations thereof will be readily apparent to those of ordinary skill in the art. Therefore, the present invention should not be considered as limited to the specific embodiment shown herein.

What is claimed is:

1. Optometer apparatus for directly measuring the refraction of the eye comprising:
    a radiation source;
    Scheiner principle means for imaging a pair of slits onto the plane of the pupil of an eye to be measured to form a retinal image, said Scheiner principle means projecting two slits of parallel light in Maxwellian view onto said plane of said pupil of said eye to be measured;
    sensor array means including a plurality of sensor elements arranged in an array, each of said sensor elements producing an electrical signal having a magnitude which is a function of incident radiation received by that sensor element, said sensor array means being responsive to incident radiation to produce a plurality of electrical signals corresponding to an element-to-element energy distribution of radiation imaged upon said sensor means; and means for imaging said retinal image upon said sensor array means.

2. The optometer apparatus according to claim 1 wherein said means for imaging said retinal image upon said sensor means comprises:

lens means having a predetermined focal length; and imaging tube means disposed intermediate said lens means and said sensor array means, said imaging tube means being in optical communication with each of said lens means and said sensor array means and having an axial length greater than said predetermined focal length to form a conjugate of said retinal image upon said sensor array means.

3. A method for directly measuring the refraction of the eye comprising the steps of:

projecting two slits of parallel light in Maxwellian view onto the plane of a pupil of an eye to be measured to form a retinal image thereof;

imaging said retinal image upon sensor array means; and producing from said sensor array means, in response to incident radiation, a plurality of electrical signals corresponding to a point-to-point energy distribution of the retinal image applied to said sensor array means.

4. The method according to claim 3 wherein said step of projecting includes the steps of:

filtering radiation from source means through an infrared filter means;

collimating said radiation from said source means; and imaging said infrared, collimated radiation upon a pair of slits in optical communication with an eye to be tested.

5. The method according to claim 3 wherein the step of imaging includes the steps of:

applying said retinal image to lens means in optical communication with said sensor array means; and disposing said sensor array means at a greater distance than the focal length of said lens means to apply the conjugate of said retinal image to said sensor array means.

6. The method according to claim 5 wherein the step of disposing is achieved by positioning tube means intermediate said lens means and said sensor array means in optical communication therewith, said tube means having a greater length than the focal length of said lens means.

7. Optometer apparatus for directly measuring the refraction of the eye comprising:

a radiation source;

means for imaging a pair of slits onto the plane of the pupil of an eye to be measured to form a retinal image;

sensor array means including a plurality of sensor elements arranged in an array, each of said sensor elements producing an electrical signal having a magnitude which is a function of incident radiation received by that sensor element, said sensor array means being responsive to incident radiation to produce a plurality of electrical signals corresponding to an element-to-element energy distribution of radiation imaged upon said sensor means;

lens means having a predetermined focal length; and imaging tube means disposed intermediate said lens means and said sensor array means, said imaging tube means being in optical communication with each of said lens means and said sensor array means and having an axial length greater than said predetermined focal length to form a conjugate of said retinal image upon said sensor array means.

8. The optometer apparatus according to claim 7 wherein said means for imaging a pair of slits upon the plane of the pupil of an eye to be measured comprises:

first and second collimating lens means disposed between and in light communication with said source means and the position of an eye to be measured; and plate means having a pair of Scheiner principle slits therein disposed intermediate and said first and second collimating lens and in light communication therewith.

9. The optometer apparatus according to claim 8 additionally comprising:

concave mirror means disposed behind said source means, said concave mirror means acting to receive radiation from portions of said radiation source, to reflect said radiation from the rear of said source means and to focus said radiation onto the plane of said source means to increase said radiation being directed onto said first lens means;

infrared filter means disposed intermediate said radiation source and said first lens means, said infrared filter means acting to absorb a substantial portion of the visible spectrum of radiation applied thereto and further conveying infrared radiation toward said first lens means; and beam splitter means disposed intermediate said second lens means and said position of an eye being measured, said beam splitter means acting to convey collimated, infrared radiation from said second lens means to said position of the plane of said pupil and radiation corresponding to a retinal image from said eye to be measured to said sensor array means.

* * * * *

UNITED STATES PATENT AND TRADEMARK OFFICE
CERTIFICATE OF CORRECTION

PATENT NO. : 4,162,828
DATED : July 31, 1979
INVENTOR(S) : Joseph N. Trachtman

It is certified that error appears in the above-identified patent and that said Letters Patent are hereby corrected as shown below:

Column 7, line 30, "1-5 volts," should read "0-5 volts,".

Signed and Sealed this

Twentieth Day of November 1979

[SEAL]

Attest:

RUTH C. MASON
Attesting Officer

LUTRELLE F. PARKER
Acting Commissioner of Patents and Trademarks